United States Patent [19]
Chase

[11] Patent Number: 5,924,580
[45] Date of Patent: Jul. 20, 1999

[54] ROTATIONAL CADAVER SYSTEM

[75] Inventor: David O. Chase, Erie, Pa.

[73] Assignee: Shandon Inc., Erie, Pa.

[21] Appl. No.: 08/717,104

[22] Filed: Sep. 20, 1996

[51] Int. Cl.$^6$ ..................................................... A47F 5/00
[52] U.S. Cl. .................... 211/131.2; 211/1.54; 211/1.55; 211/165; 312/135; 312/267
[58] Field of Search .................. 211/164, 165, 211/1.54, 1.55, 121, 131.2; 312/135, 266, 267, 116

[56] References Cited

U.S. PATENT DOCUMENTS

| 125,928 | 4/1872 | Blake | 211/131.2 X |
|---|---|---|---|
| 1,281,105 | 10/1918 | Unger | 211/164 |
| 1,785,954 | 12/1930 | Hayes | 211/164 X |
| 1,830,373 | 11/1931 | Schmidt | 211/164 |
| 2,829,780 | 4/1958 | Boor | 211/121 |
| 3,674,155 | 7/1972 | Kessler | 211/1.54 |
| 4,303,283 | 12/1981 | Mueller | 211/164 X |
| 5,039,180 | 8/1991 | Lemons | 312/267 |
| 5,248,049 | 9/1993 | Murphy | 211/131.2 X |

*Primary Examiner*—Robert W. Gibson, Jr.
*Attorney, Agent, or Firm*—The Bilicki Law Firm, P.C.

[57] ABSTRACT

A rotational cadaver system is disclosed which incorporates a rotational storage rack. The rotational storage rack includes a first and second shaft and two wheels mounted thereto. The shaft is rotationally mounted on a plurality of legs. A number of branches are radially secured to each wheel and arms are pivotally secured to each branch. The arms include means for receiving a tray upon which a cadaver may be placed. The trays includes means for engagement with mechanical placement and retrieval means. The tray also include means for securing them to various types of autopsy tables. A motor is also provided for turning the shaft varying the position of the cadavers. A method is also disclosed for utilizing the system in conjunction with the performance of an autopsy.

8 Claims, 11 Drawing Sheets

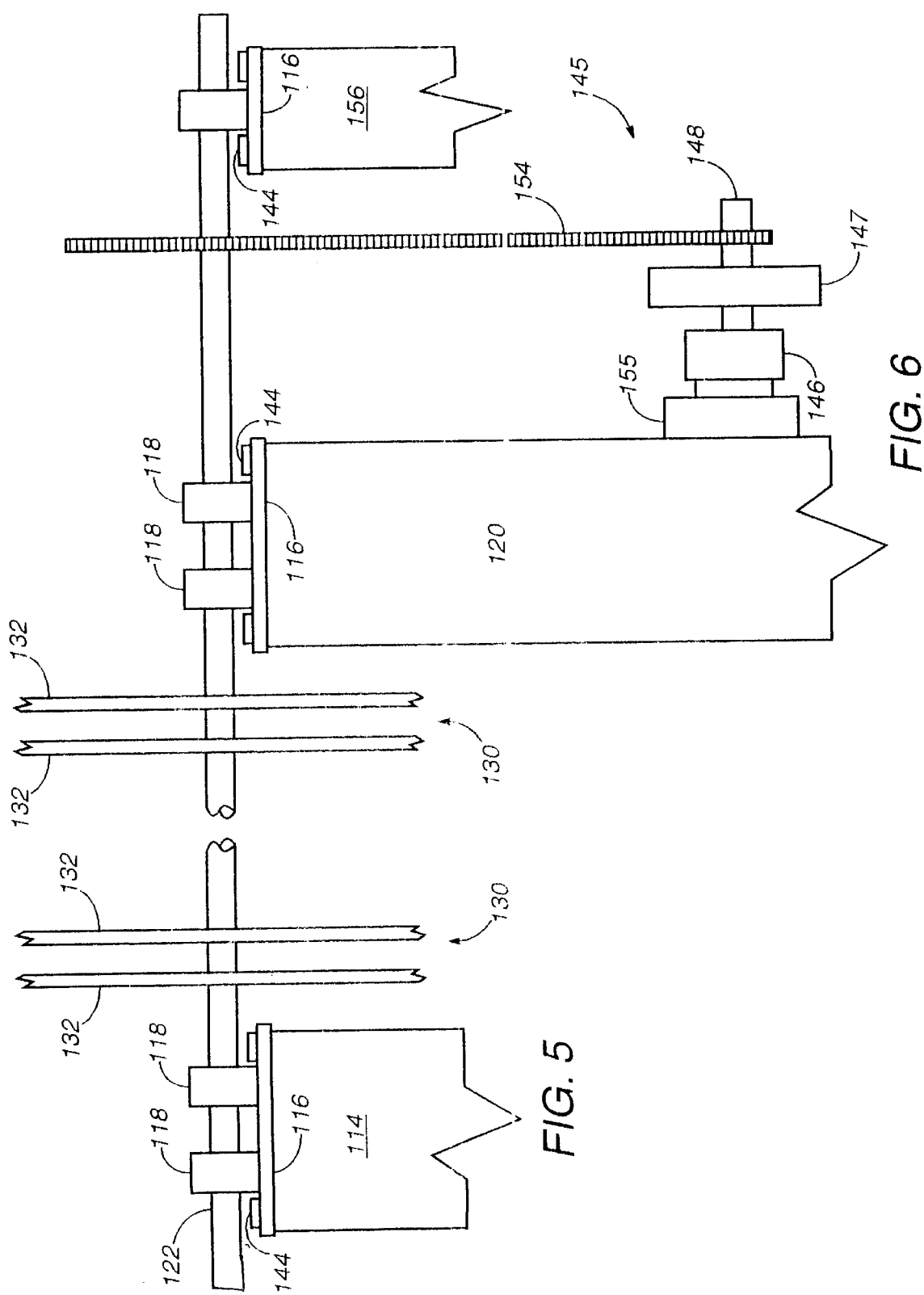

ROTATIONAL CADAVER SYSTEM

BACKGROUND OF THE INVENTION

The present invention relates to generally to refrigerated housings and more particularly to those refrigerated housings suited for the storage of cadavers. The invention is specifically related to a rotational cadaver system which utilizes a rotational storage rack to store the cadavers.

It is well known that hospitals utilizes refrigerated compartments to store cadavers prior and subsequent to the performance of an autopsy. This is necessary to preserve the body and prolong the natural decomposition process which would normally take place without refrigeration.

Typical cadaver refrigeration units also utilize a telescoping tray assembly with each cadaver stored on an individual tray stored within the refrigeration unit. In order to remove a cadaver from such an assembly, it is typically required that an orderly or other personnel physically lift the cadaver and place it on a cart. The reverse is also true when the cadaver is to be placed in the refrigeration unit. Such activities can often be the cause of work related injuries, especially in cases where the cadaver to be moved is heavy. While numerous storage means exist, none are particularly suited for use with cadavers in a post mortem setting. Accordingly, there is a need for efficient storage and retrieval of cadavers.

The prior art discloses numerous refrigerated systems and rotational storage devices. For example, U.S. Pat. No. 143,059 issued on Sep. 23, 1873 to Camp discloses a refrigerator which is constructed such that the interior parts may be readily removed for cleaning. The refrigerator includes a hollow perforated shaft with four-armed plates or spiders and a plurality of swinging shelves. The shelves are pivotally mounted to the four-armed plates so that items may be readily placed or removed from the shelves.

U.S. Pat. No. 1,785,954 issued on Dec. 23, 1930 to Hayes discloses a dispensing refrigerator which is mainly designed to dispense bottled beverages. The refrigerator includes a rotary member which is disposed in a cooling chamber. A plurality of racks or trays are suspended to the rotary member and are capable of holding the bottles or articles placed therein. The racks are connected to the rotating member such that they assume an upright position irrespective of their location relative to the rotary member.

U.S. Pat. No. 2,592,038 issued on Apr. 8, 1952 to Kimsey discloses a refrigerated display case. The display case includes a plurality of supports which are circumferentially spaced. The supports pivotally suspend a plurality of food trays therefrom.

U.S. Pat. No. 3,269,569 issued on Aug. 30, 1966 to Brauner discloses a rotary vehicle parking apparatus. The apparatus includes a frame structure which is rotatably supported between pins or stub shafts. The frame structure has a plurality of platforms which are each adapted to support a vehicle. Means are provided for rotating the structure in order to bring each of the platforms to ground level in a successive manner.

U.S. Pat. No. 3,356,233 issued on Dec. 5, 1967 to De Filippis discloses a rotatable parking apparatus for motor vehicles. The apparatus includes a rotatable portion which includes a wheel housing and individual carriers that are supported by the wheel housing. The individual carriers are pivotally supported in order to facilitate loading and unloading the vehicles.

U.S. Pat. No. 3,927,772 issued on Dec. 23, 1975 to Borner discloses a vehicle parking and rotary elevator assembly. The assembly includes a wheel which has a pair of axially spaced, coaxial ring gears. The ring gears are supported for rotation about a common horizontal axis. Vehicle carrying platforms are pivotally suspended to the ring gears. A plurality of vehicle parking floors extend into an edgewise adjoining relationship relative to the circumferential periphery of the ring gears and at different levels relative to the common axis. Parking floor portions are arranged radially and centrally relative to the platforms. Idler rollers are used to support the ring gears at the top and bottom thereof.

U.S. Pat. No. 4,952,112 issued on Aug. 28, 1990 to Piacenza discloses a mechanical storage multi-level carpark the carpark includes a gantry structure formed by a set of uprights and cross-beams. The uprights and cross-beams define a space inside of which a vertical carousel structure is supported. The vertical carousel structure is further provided with car housing supports.

U.S.S.R. Patent # 452,730 published on December 1974 discloses a refrigerator chamber for biological testing. The chamber has a heat insulated housing and rotating sample containers and an evaporator. The heat insulated housing is cylindrical and the evaporators are evenly placed within the housing. A drive shaft rotates the container system while a plurality of arms are used to support the cradles. The cradles are hinged to the arms so that they continually occupy a horizontal position.

None of the prior art is seen to describe the present invention as claimed. Therefore, a rotational cadaver system which facilitates the storage and retrieval of cadavers would be beneficial.

OBJECTS AND SUMMARY OF THE INVENTION

Accordingly, it is an object of this invention to provide a rotational storage rack capable of supporting multiple items.

It is another object of this invention to provide an autopsy assembly.

It is yet another object of this invention to provide a rotational cadaver system utilizing a rotational storage rack.

It is a further object of this invention to provide a rotational storage system which utilizes a stacker for placement and removal of cadavers from the rotational storage rack.

It is yet a further object of this invention to provide a means for mechanically turning the rotational storage rack.

It is a still further object of this invention to provide a method of processing a cadaver.

In accordance with an object of this invention, a rotational storage rack is provided for removably storing a plurality of items. The rotational storage rack is especially suited for the storage of cadavers. The rotational storage rack includes a base, two legs, a first shaft, and a second shaft.

The base has a generally rectangular shape with a hollow interior. The rectangular shape of the base defines two long sides and two short sides. The first leg is vertically positioned at about the midpoint of one of the short sides of the base. The first leg is then secured to the corresponding short side of the base. The second leg is similarly positioned and secured to the remaining short side of the base.

The first and second shafts are respectively positioned proximate the first and second legs in a horizontal manner which is parallel to the long sides of the base. The first and second shafts are then rotatably mounted to the first and second legs. A spool is mounted on the first and second shafts. The length of the spool is shorter than the distance between the first and second legs and each of its ends terminates in an outwardly extending flange. A wheel is positioned at each end of the spool and secured to a corresponding flange. The wheels are also secured to the first and second shafts.

A plurality of branches are secured to each of the wheels. Each of the wheels receives the same number of branches. The wheels are further oriented such that when viewed along the centerline of the first and second shafts, each branch from the first wheel is aligned with a corresponding branch from the second wheel. An arm is pivotally attached at one end to each of the branches. A number of trays are provided for supporting the items being stored. The trays are designed with a predetermined length corresponding to the distance between a corresponding pair of arms from the first and second wheel. Consequently, each tray is supported by one pair of arms.

In accordance with another object of the invention, an autopsy assembly is provided which includes an autopsy tray, an autopsy cart, and an autopsy station. The autopsy tray includes a plurality of apertures while the autopsy cart includes a plurality of receptors for insertably engaging the autopsy tray. The autopsy cart also includes a latching mechanism for securing it to the autopsy station. The autopsy tray includes a plurality of peripherally disposed suction and irrigation ducts. Quick disconnect fittings integrally attached to the autopsy tray are used for providing fluid and ventilation during the autopsy.

In accordance with another object of the invention, a rotational cadaver system is provided which utilizes a rotational storage rack. The rotational cadaver system consists of a refrigerated housing, a rotational storage rack, means for removing the contents of the rotational storage rack, a cadaver carrier, an autopsy cart, and an autopsy station.

The rotational storage rack of the system includes a base which has a generally rectangular shape with a hollow interior, thus defining two long sides and two short sides. The first and second legs are vertically positioned at about the midpoint of each of the short sides of the base and respectfully secured thereto. The first and second shafts are respectively positioned proximate the first and second legs in a horizontal manner which is parallel to the long sides of the base. The first and second shafts are then rotatably mounted to the first and second legs.

A plurality of bearings are provided to facilitate the rotational mounting of the first and second shafts. Two bearings are secured to each the first leg and the second leg by a bearing mount. The first and second shafts are then inserted through the inner races of the bearings and allowed to ride thereon.

A spool is mounted on the first and second shafts. The spool has ends which terminate in an outwardly extending flanges. A wheel is positioned at each end of the spool and secured to a corresponding flange. Each wheel is further secured to the first and second shafts, respectively.

A plurality of branches is secured to each of the wheels. Each of the wheels receives the same number of branches and, when viewed along the centerline of the first and second shafts, each branch from the first wheel is aligned with a branch from the second wheel. An arm is pivotally attached at one end to each of the branches. A number of trays of predetermined length are provided for supporting the cadavers being stored. The length of each tray corresponds to the distance between each corresponding pair of arms on the first and second wheel. Thus, each tray is supported by a corresponding pair of arms. Each tray further includes a plurality of apertures. In preferred embodiments of the invention, each wheel is comprised of a first and second plate and the branches are sandwiched therein.

The cadaver carrier of the system includes a frame which has a generally rectangular shape and defines two long sides and two short sides. The cadaver carrier also includes four upstanding legs, each of which is attached at one corner of the base in a vertical manner. Casters are attached to the lower end of each leg in order to facilitate movement. Most preferably, the cadaver carrier includes a rigid cover and shroud to shield a hospital's patients, employees and visitors from viewing the outline of a cadaver as it is being transported through a hospital to the hospital's morgue. A plurality of receptors are provided to correspondingly engage the apertures contained in the tray.

The autopsy cart of the system includes a frame which has a generally rectangular shape and defines two long sides and two short sides. The autopsy cart also includes four upstanding legs, each of which is attached at one corner of the base in a vertical manner. Casters are attached to the lower end of each leg in order to facilitate movement. A plurality of receptors are provided to correspondingly engage the apertures contained in the tray. The autopsy cart also includes means for securing it to the autopsy station. Furthermore, the two upstanding legs of the autopsy cart, to which the securing means are attached, are most preferably 1 inch shorter than the opposite two upstanding legs. As such, the tray is sloped in a downward direction toward the autopsy station when the autopsy cart is secured thereto, for purposes of facilitating drainage of fluids arising during the course of an autopsy.

In accordance with another object of the invention, a stacker is provided as the means for placing and removing the contents of the rotational storage rack. The stacker of the system is designed as a hydraulic lifting apparatus and may be a forklift in preferred embodiments of the invention. The stacker includes wheels, casters, or other appropriate means of facilitating movement along a surface. The stacker may also include means for an operator to govern the movement of the stacker, such as a steering mechanism or a drive control mechanism. The stacker has loading means upon which objects may be positioned. The stacker further includes means for lifting and lowering objects, such as the tray of the present system, placed upon the loading means. In preferred embodiments of the rotational cadaver system, the loading means of the stacker is a pair of prongs which are spaces apart by a predetermined distance. Each of the trays includes a pair of channels which are spaced apart by a distance corresponding to the distance between the prongs of the stacker.

In accordance with another object of the invention, a motor is provided for turning the rotational storage rack. The motor includes means for selectively turning it on and off, and means for transmitting its output to the second shaft of the rotational storage rack. In order to transmit its output to the rotational storage rack, the motor includes a drive shaft which is in turn connected to a trans reduction case for reducing the effective velocity of the drive shaft. A drive gear is mounted on the output shaft of the trans reduction case while a driven gear is mounted on the second shaft of the rotational storage rack. Means such as belt or chain are provided to interrelate the drive gear and the driven gear.

In accordance with another object of the invention, a method is provided for processing a cadaver for an autopsy. The first step of the process is to place the cadaver in a refrigerated housing for a predetermined length of time, or until an appropriate official is ready to perform the autopsy. When appropriate, the cadaver is removed from the refrigerated housing. In order to remove the proper cadaver, it may be necessary to turn the rotational storage stack so that the tray containing the required cadaver is properly positioned for removal. Next, the tray supporting the cadaver is removed from the rotational storage rack and placed on an autopsy cart. The autopsy cart may then be moved to the location where the autopsy is to be performed. The autopsy cart is then secured to the autopsy station, at which time an autopsy can be performed.

The above and many other objects, features and advantages of this invention will be better understood from the ensuing description of selected preferred embodiments, which should be read in conjunction with the accompanying Drawing.

BRIEF DESCRIPTION OF THE DRAWING

FIG. 5 is an enlarged front elevational view of the first leg of the rotational storage rack used in the rotational cadaver system.

FIG. 6 is an enlarged front elevational view of the second leg and motor of the rotational storage rack used in the rotational cadaver system.

DESCRIPTION OF THE PREFERRED EMBODIMENTS

Figure 1:
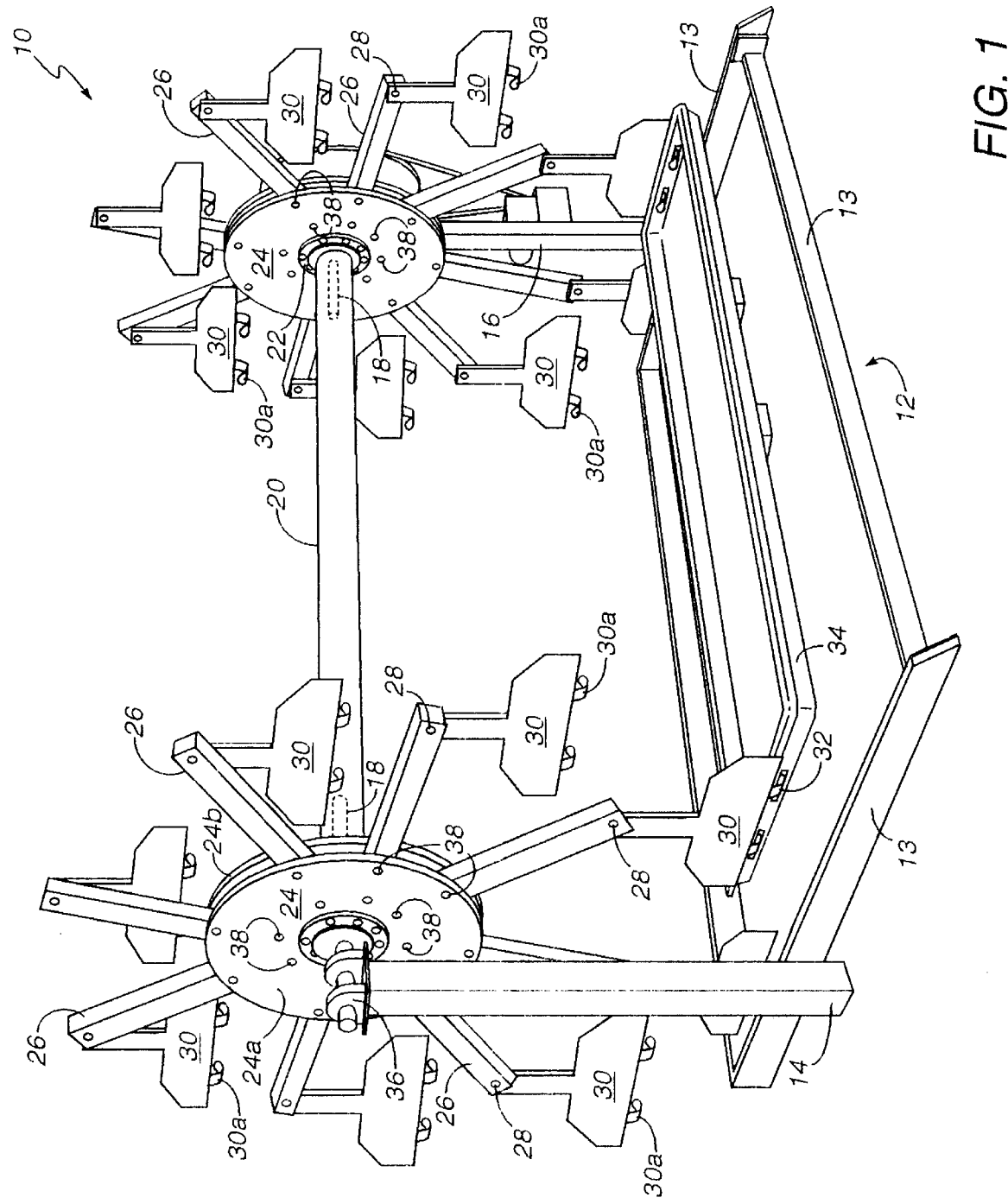
FIG. 1 is a perspective view of the rotational storage rack of the present invention.

With reference to the Drawing, and initially to FIG. 1, there is shown a rotational storage rack 10 in accordance with the present invention. The rotational storage rack 10 includes a base 12 which has a generally rectangular shape. The base 12 is formed from a plurality of members 13 which are rigidly secured to each other. The rectangular shape of the base 12 defines two short sides and two long sides.

A first leg 14 is vertically positioned at about the midpoint of one of the short sides of the base 12. The first leg 14 is then secured to the corresponding short side of the base 12 by appropriate means such as a weld. The second leg 16 is similarly positioned at about the midpoint of the remaining short side of the base 12 and secured thereto. The first and second shafts 18 are respectively positioned proximate the first and second legs 14, 16 in a horizontal manner which is parallel to the long sides of the base 12. The first and second shafts 18 are then rotatably mounted to the first and second legs 14, 16.

A spool 20 is mounted on the first and second shafts 18. Furthermore, each of the ends of the spool 20 terminates in an outwardly extending flange 22. The flanges 22 at the ends of the spool 20 extend along a plane which is perpendicular to the centerline of the first and second shafts 18 and the spool 20. A wheel 24 is positioned at each end of the spool 20 and secured to a corresponding flange 22. Wheel 24 is seen to be comprised of a first and second plate 24(a), 24(b). The wheels 24 are also secured to the first and second shafts 18.

Figure 3:
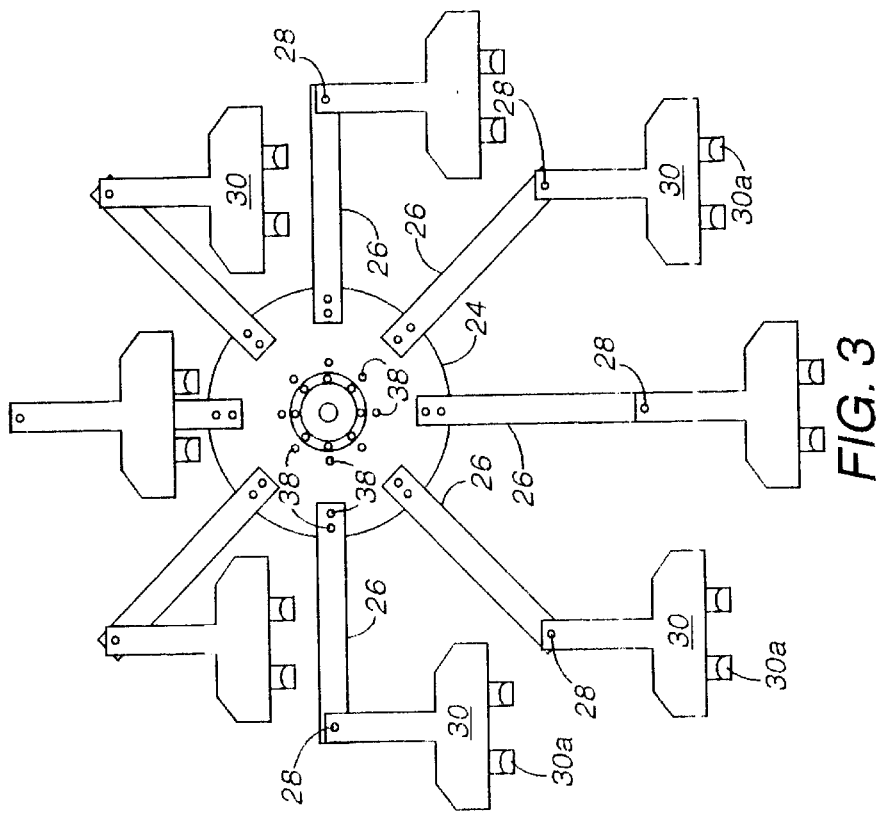
FIG. 3 is a perspective view of an alternative embodiment of the wheel of the rotational storage rack.

With continued reference to FIG. 1 and particular reference to FIG. 3, the wheels 24 are shown to be secured to the flanges 22 with fasteners 38. This, however is not a requirement. The wheels 24 may be secured in numerous ways including welding, which is the preferred means for securing. A plurality of branches 26 are sandwiched between first and second plates 24(a) and 24(b). Fasteners 38 such as bolts are used to secure each branch 26 between first and second plates 24(a), 24(b). Each of the wheels 24 receives the same number of branches 26. The branches 26 are oriented in a radial manner with respect to the center of their respective wheel 24. Furthermore, the wheels 24 and branches 26 are oriented and secured in such a manner that when viewed along the centerline of the first and second shafts 18, each branch 26 from the first wheel 24 is aligned with a corresponding branch 26 from the second wheel 24. An arm 30 is pivotally attached to each of the branches 26 via a pin 28. A number of trays 34 are provided for supporting the items being stored. The trays 34 are designed with a predetermined length corresponding to the distance between the pairs of arms 30 in the first and second wheel 24. Each tray 34 further includes a plurality of apertures disposed along two of its sides.

A plurality of receptors 30(a) are rigidly secured to the free end of each arm 30 in order to support the trays 34. As illustrated in FIGS. 1 and 3, the receptors are generally hook shaped. This allows the receptors 30(a) to insertably engage the apertures contained in the tray 34. Accordingly, each tray 34 is supported by one arm 30 from the first wheel 24 and a corresponding arm 30 from the second wheel 24. As seen by intuitively examining the different branches and arms 26, 30 in FIG. 3, the pins 28 allow the arms 30 to pivot with reference to the branches 26. As the first and second shafts 18 are rotated, they correspondingly rotate the wheels 24. The arms 30, in turn pivot in accordance to the degree of rotation so as to continually maintain the trays 34 in a horizontal manner, thereby not spilling the contents of the trays 34.

Figure 2:
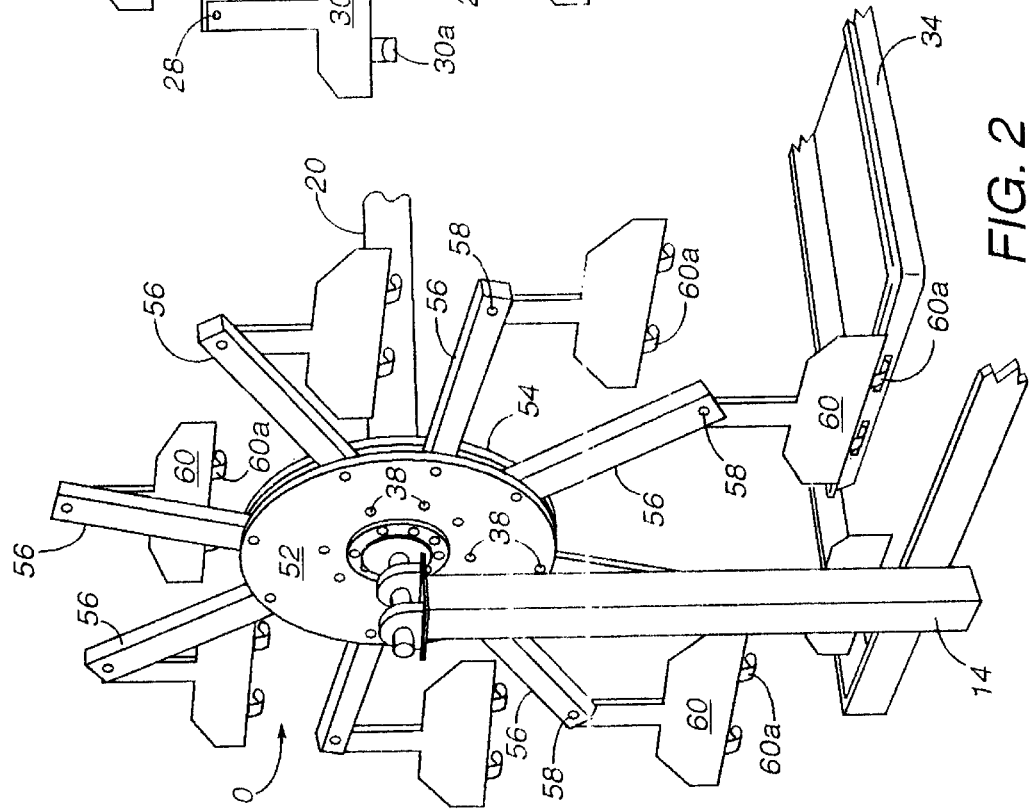
FIG. 2 is a front elevational view of the wheel of the rotational storage rack.

FIG. 2 illustrates a preferred embodiment of the wheel of the present invention. The wheel 50 is seen to be comprised of a first and second plate 52, 54. A plurality of branches 56 are sandwiched between the first and second plates 52, 54. Fasteners 38 such as bolts are used to secure each branch rigidly between the two plates 52, 54. Alternatively, the branches 56 could be welded to the plates 52, 54. Each branch 56 is positioned in a radial manner with respect to the center of the first and second plates 52, 54. The first and second (not shown) shafts 18 extend through each wheel 50. The second plate 54 of the wheel 50 is secured to the flange 22 of the spool 20 by a plurality of fasteners 38. The first and second plates 52, 54 of the wheel 50 are respectively secured to the first and second shafts 18, preferably by welding. Each branch 56 also includes an arm 60 which is pivotally mounted thereto via a pin 58. Each arm further includes a plurality of receptors 60(a) which are generally hook shaped in order to effectuate support of the tray 34.

Figure 4:
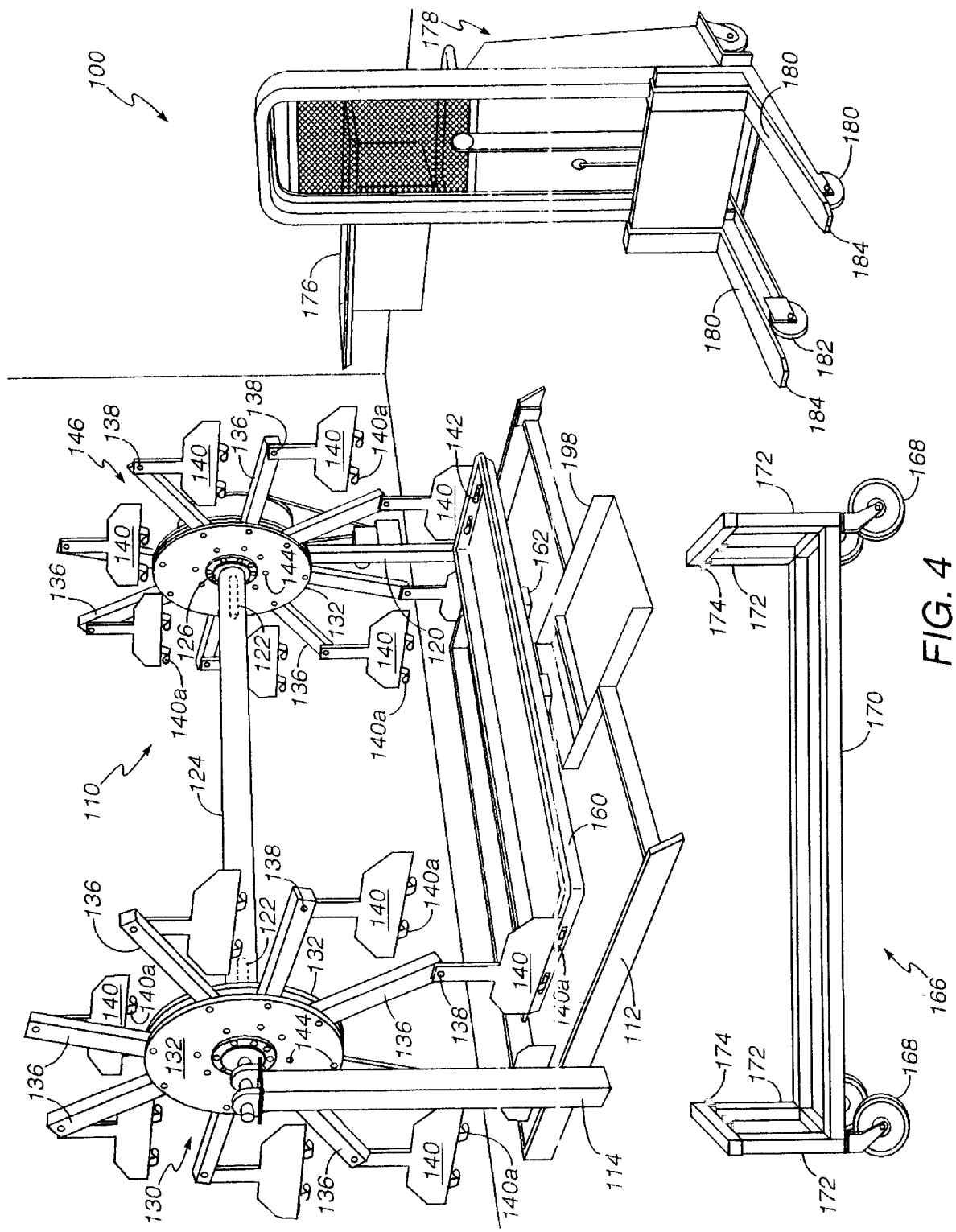
FIG. 4 is a perspective view of a rotational cadaver system according to the present invention.

Turning to FIG. 4, a rotational cadaver system 100 which utilizes a rotational storage rack 110 is illustrated. The rotational cadaver system 100 additionally includes a refrigerated housing (not shown), means for removing the contents of the rotational storage rack, a cadaver carrier 166, and an autopsy cart (not shown).

The rotational storage rack 110 of the system includes a base 112 which has a generally rectangular shape and a hollow interior. The rectangular shape of the base 112 accordingly defines two long sides and two short sides. The rotational storage rack 110 also includes a first and second leg 114, 120 which are each vertically positioned at about the midpoint of each of the short sides of the base 112 and appropriately secured thereto by welding. A first and second shaft 122 are horizontally positioned proximate the first and second legs 114, 120. As seen in FIG. 4, the orientation of the first and second shafts 122 is parallel to the long sides of the base 112. The first and second shafts 122 are then rotatably mounted to the first and second legs 114, 120, respectively.

As seen more particularly with reference to FIG. 5, a plurality of bearings 118 is used to facilitate the rotational mounting of the first shaft 122. A bearing mount 116 is used to secure the bearings 118 to the first leg 114. Each bearing 118 includes an outer race and an inner race (not shown). The outer race of each bearing 118 is rigidly secured to the bearing mount 116. The first shaft 122 is then mounted within the inner race of the bearings 118 so that it may rotate with the inner race. A plurality of fasteners 144 are used to secure the bearing mount 116 to the first leg 114. The second shaft 122 is similarly mounted to the second leg 120.

A spool 124 is mounted on the first and second shafts 122. As seen in FIG. 4, the first and second shafts penetrate a predetermined distance within the spool 124. Each of the ends of the spool 124 further terminates in an outwardly extending flange 126. A first wheel 130 is positioned at the end of the spool 124 proximate the first leg 114 and appropriately secured with fasteners 144. Similarly, a second wheel 146 is positioned at the opposite end of the spool 124, proximate the second leg 120, and secured to the corresponding flange with fasteners 144.

A plurality of branches 136 are secured to the first and second wheels 130, 146. As is apparent in FIG. 4, each of the wheels 130, 146 receives an equal number of branches 136. The branches 136 are further aligned in a radial manner with respect to their corresponding wheel, such that each branch 136 would pass through the midpoint of its corresponding wheel. Furthermore, the first and second wheels 130, 146 are cooperatively aligned such that when viewed along the centerline of the first and second shafts 122, each branch 136 from the first wheel 130 is seen to be aligned with a branch 136 from the second wheel 146. This arrangement also defines corresponding pairs of branches 136 in the rotational storage rack 110.

Referring again to FIG. 5 with particularity, the first wheel 130 is seen to be comprised of a first and second plate 132. Each of the two plates 132 is positioned on opposite sides of the branches 136 corresponding to the first wheel 130. Although various equivalent means exist, fasteners 144 are used to secure the first and second plates 132 and the branches 136 as a unitary structure. This preferred arrangement of the first wheel 130 allows the flange 126 of the spool 124 to be rigidly secured to one of the plates 132. Furthermore, the first shaft 122 is secured to each plate 132 of the first wheel 130 preferably by welding. With continued reference to FIG. 4, an arm 140 is shown attached to the end of each of the branches 136. The arms 140 are attached in a pivotal manner by means of a pin 138. The pivotal connection of the arms 140 insures that they occupy a vertical orientation regardless of their radial position with respect to the first and second wheels 130, 146. The arms 140 generally retain this orientation even as the first and second shafts 122, and consequently the first and second wheels 130, 146, are rotated. Furthermore, each arm 140 associated with the first wheel 130 is paired with an arm 140 associated with the second wheel 146.

A number of trays 160 are provided for supporting the cadavers being stored on the rotational storage rack 110. The length of the trays 160 is predetermined to be generally equivalent to the distance between each corresponding pair of arms 140 on the first and second wheels 130, 146. Thus, each tray 160 is partially supported at one end by an arm 140 from the first wheel 130 and at the other end by a corresponding arm 140 from the second wheel 146. While various means exist to provide support of the trays 160, the arms 140 are preferred to include a receptor 142 rigidly secured to their ends. The receptors 142 are positioned so that they support the trays 160 in a generally flat orientation. As illustrated in FIG. 4, the receptors 142 are generally hook shaped. In order effectuate this support, each tray 160 includes a plurality of apertures corresponding to the receptors 142. Thus, the receptors 142 of each arm 140 insertably engage the apertures in the tray 160. Since the nature of the connection of the arms 140 to the branches 136 forces the arms 140 to occupy a vertical orientation, the receptors 142 accordingly cause the trays 160 to maintain a flat orientation regardless of their position on the rotational storage rack 110. Each tray 160 further includes two channels 162 superimposed to the bottom surface thereof, with the channels 162 being spaced apart by a predetermined distance.

Figure 7:
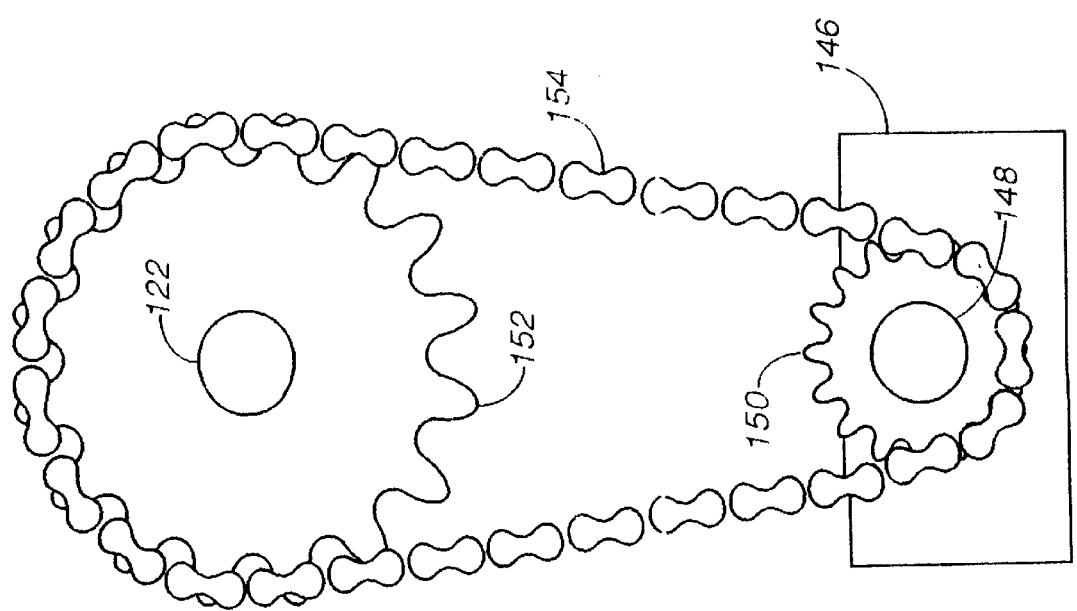
FIG. 7 is a cross-section illustrating the motor of the rotational cadaver system.

The second shaft 122 is secured to the second leg 120 in a manner similar to that of the first leg 114, as illustrated in FIG. 6. A bearing mount 116 is used to secure a plurality of bearings 118 to the second leg 120 via fasteners 144. The bearing mount 116 retains the outer races of the bearings 118 in a fixed position while allowing the inner races to rotate freely. The second shaft 122 is then mounted within the inner races of the bearings 118 and allowed to rotate in accordance therewith. FIG. 6 also shows a mechanical drive 145 system which is the preferred method of turning the rotational storage rack 110. The mechanical drive system includes a motor 146 and means for transmitting the output of the motor 146 to the second shaft 122. The motor 146 is rigidly secured to the second leg 120. The motor 146 also includes a drive shaft which extends therefrom. A trans reduction case 147 receives the drive shaft of the motor 146 and serves as a means of reducing the rotational velocity of the motor 146. The trans reduction case 147 includes an output shaft 148 which has a drive gear 150 mounted thereon, as seen with additional reference to FIG. 7. In preferred embodiments of the invention, the trans reduction case 147 achieves a 1200:1 reduction ration. The second shaft 122 includes a driven gear 152 mounted thereon. A chain 154 is used to interrelate the output of the output shaft 148 to the driven gear 152 and consequently the second shaft 122. As seen in the illustration, the drive gear 150 and the driven gear 152 each include a plurality of sprockets in order to mesh with the chain 154. It should be appreciated, however, that various other transmission means exist, such as a system employing a plurality of pulleys and a belt.

In preferred embodiments of the invention, a third leg 156 is also provided for further supporting the second shaft 122. The third leg 156 is positioned in a similar manner as the first and second legs 114, 120 beneath the second shaft 122. A support block 155 is rigidly secured to the second and third legs 120, 156. The motor 146 is subsequently secured to the support block 155. A bearing mount 116 secures a bearing 118 to the third leg 156 via fasteners 144. The terminal end of the second shaft 122 is mounted on the inner race of the bearing 118 on the third leg 156. The third leg 156 is provided in order to relieve some of the stress which is placed on the bearings 118 mounted on the second leg 120. The stresses arise due to the tension placed on the second shaft 122 from the drive train. The motor also includes switching means (not shown) for selectively providing power thereto, and consequently turning the first and second shafts 122 and the first and second wheels 130, 146 in order to position a selected cadaver for removal. Furthermore, braking means are provided so that the rotational storage rack 110 will not move while the power is selectively switched off.

Figure 8:
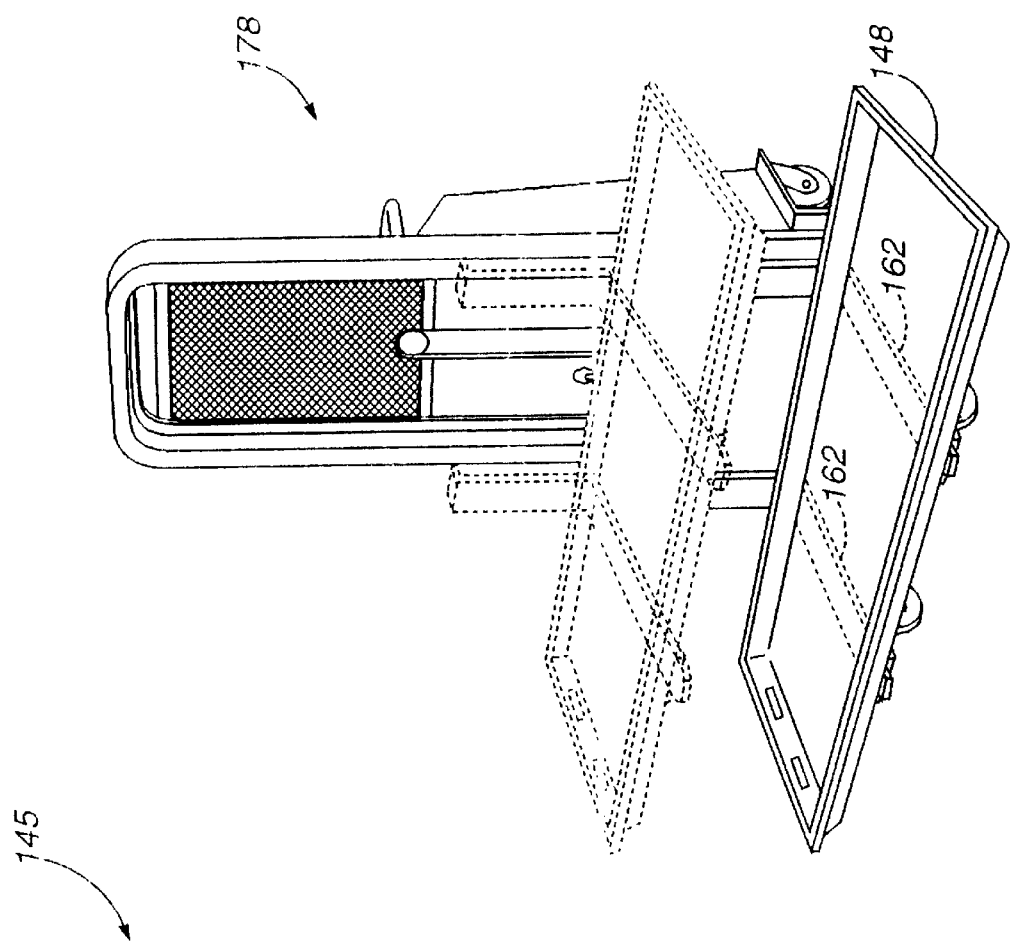
FIG. 8 is a perspective view of the tray being supported by a stacker.

FIG. 8 illustrates the stacker 178 of the rotational cadaver system 100. The stacker includes a plurality of casters 182 to facilitate movement along the ground. The stacker 178 also includes two pronged extensions 180 for supporting the trays 160. Each pronged extension 180 has a tapered end 184. The distance between each prong 180 of the stacker 178 corresponds to the distance between the channels 162 of the trays 160. In order to remove the trays from the receptors 142, the prongs 180 of the stacker 178 engage the channels 162 of the trays 160. The tapered ends 184 help facilitate and guide the prongs 180 into the channels 162. As illustrated by the phantom lines in FIG. 8, the stacker 178 is capable of vertically adjusting the position of the prongs 180 so that it may remove or place the trays 160 from or onto the receptors 142.

Figure 9:
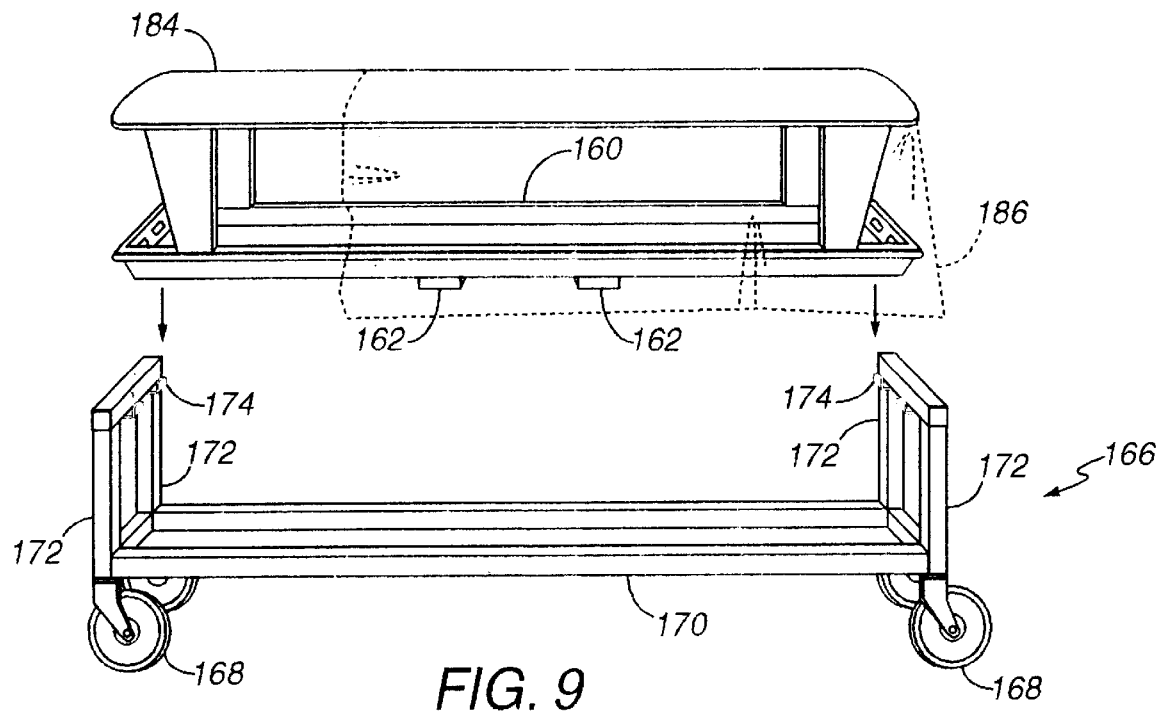
FIG. 9 is a perspective view of the cadaver carrier of the rotational cadaver system.

Once removed from the rotational storage rack 110, the tray 160 may be placed on a cadaver carrier 166, as illustrated in FIG. 9. The cadaver carrier 166 includes a frame 170 which is formed from a plurality of rigid members. The frame 170 has a generally rectangular shape which defines two long sides and two short sides. The cadaver carrier 166 also includes four upstanding legs 172, each of which is attached at one corner of the frame 170 in a vertical manner. Casters 168 are attached to the lower ends of each upstanding leg 172 in order to facilitate movement. A plurality of receptors 174 are secured to the short sides of the frame 170. The receptors 174 allow the tray 160 to be placed securely on the cadaver carrier 166. The cadaver carrier 166 also includes a rigid cover 184 and a shroud 186. The cover 184 and shroud 186 are used to give the perception that a box or crate is being transported as opposed to a cadaver.

Figure 10:
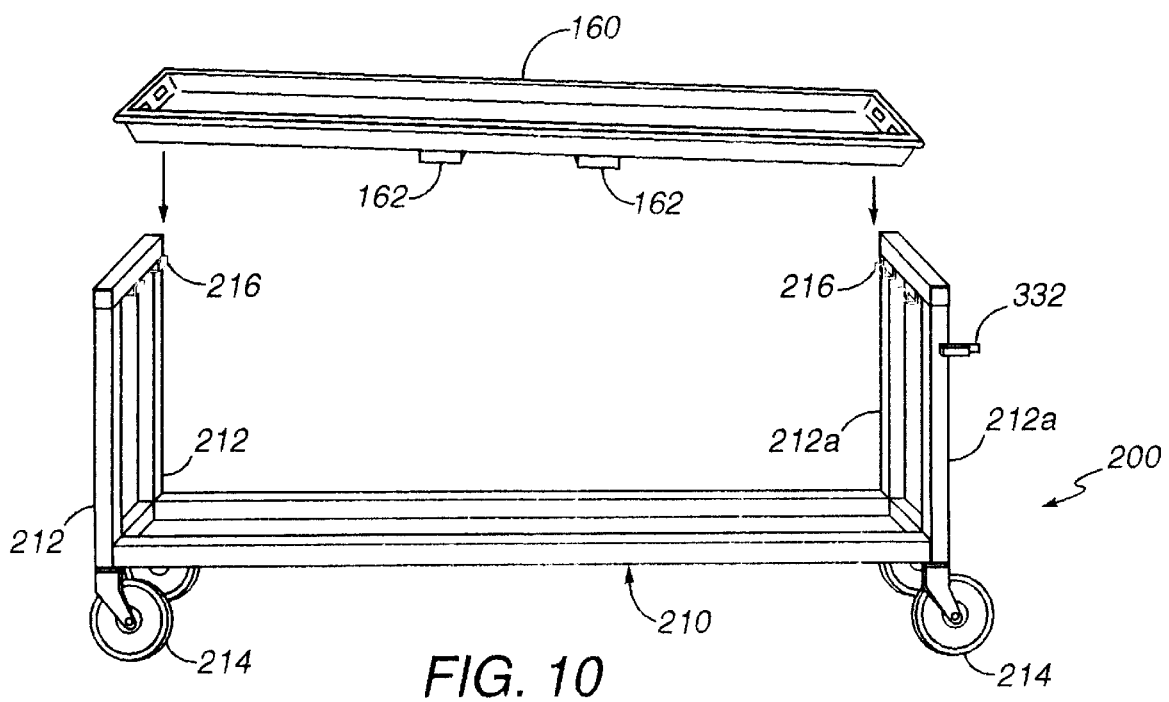
FIG. 10 is a perspective view of the autopsy cart of the rotational cadaver system.

Turning again to FIG. 4, the rotational storage rack 110 is seen to include a pathway generally indicated by the numeral 198. The pathway 198 is sized to correspond to the width of the stacker 178. In operation, the stacker 178 is moved into the pathway 198 in order to place or remove a tray 174. As the stacker 178 enters the pathway, it is forced into an alignment which facilitates the engagement of the prongs 180 with the channels 172 of the trays 174. Once removed from the rotational storage rack 110, the tray 160 may be taken to the location of the autopsy and placed on an autopsy cart 200, which may be seen more particularly with reference to FIG. 10. The autopsy cart 200 is then secured to the autopsy station. The autopsy cart 200 includes a frame 210 which is formed from a plurality of rigid members. The frame 210 has a generally rectangular shape which defines two long sides and two short sides. The autopsy cart 200 also includes 2 sets of two upstanding legs 212 and 212($a$), each of which is attached at one corner of the frame 210 in an vertical manner. Upstanding legs 212($a$) are most preferably 1 inch shorter than upstanding legs 212. As such, tray 160 is sloped in a downward direction toward latching mechanism 332 and autopsy station 250, for purposes of facilitating the drainage of fluids arising during the course of an autopsy. Casters 214 are attached to the lower ends of each upstanding leg 212 in order to facilitate movement. A plurality of receptors 216 are secured to the short sides of the frame 210. The receptors 174 allow the tray 160 to be placed securely on the autopsy cart 200. The autopsy cart 200 further includes means for securing it to various types of autopsy stations, including stand-alone and wall mounted units.

Figure 11:
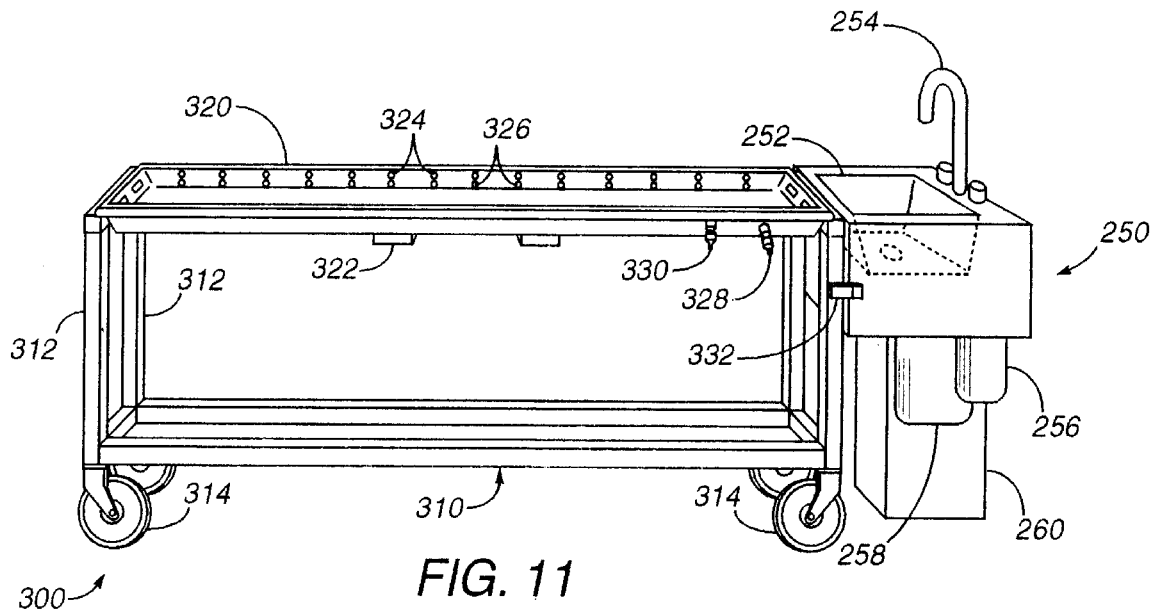
FIG. 11 is a perspective view of a preferred embodiment of an autopsy assembly which includes a free standing autopsy station.
Figure 12:
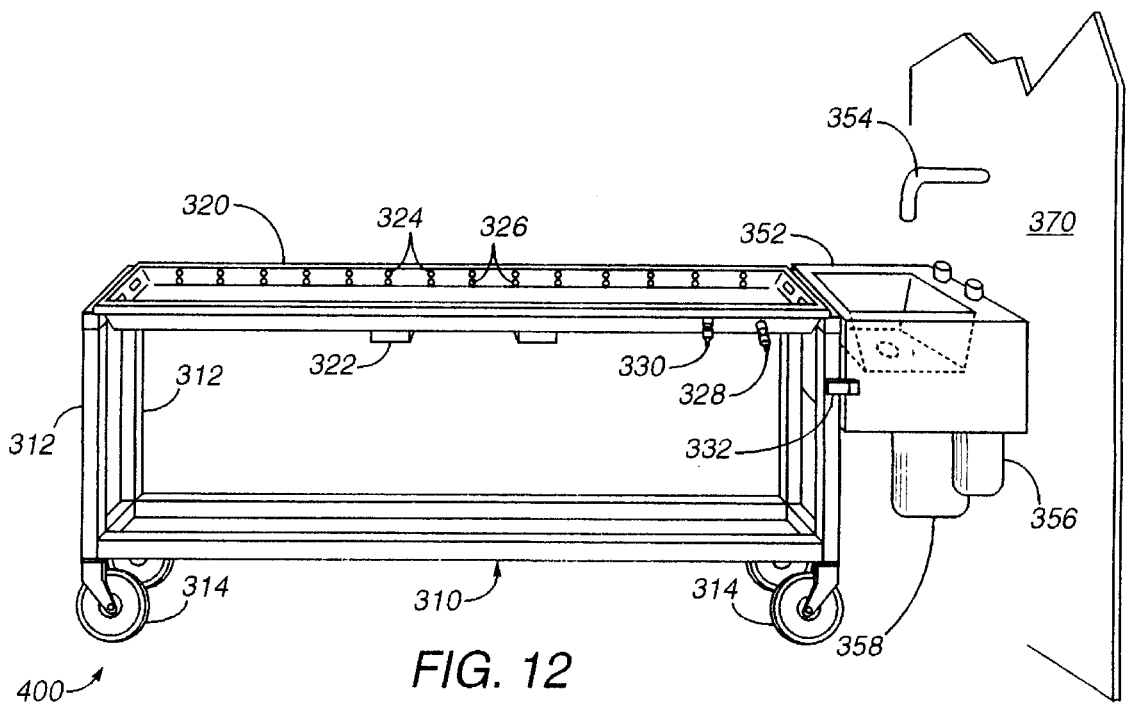
FIG. 12 is a perspective view of a preferred embodiment of an autopsy assembly which includes a wall mounted autopsy station.
Figure 13:
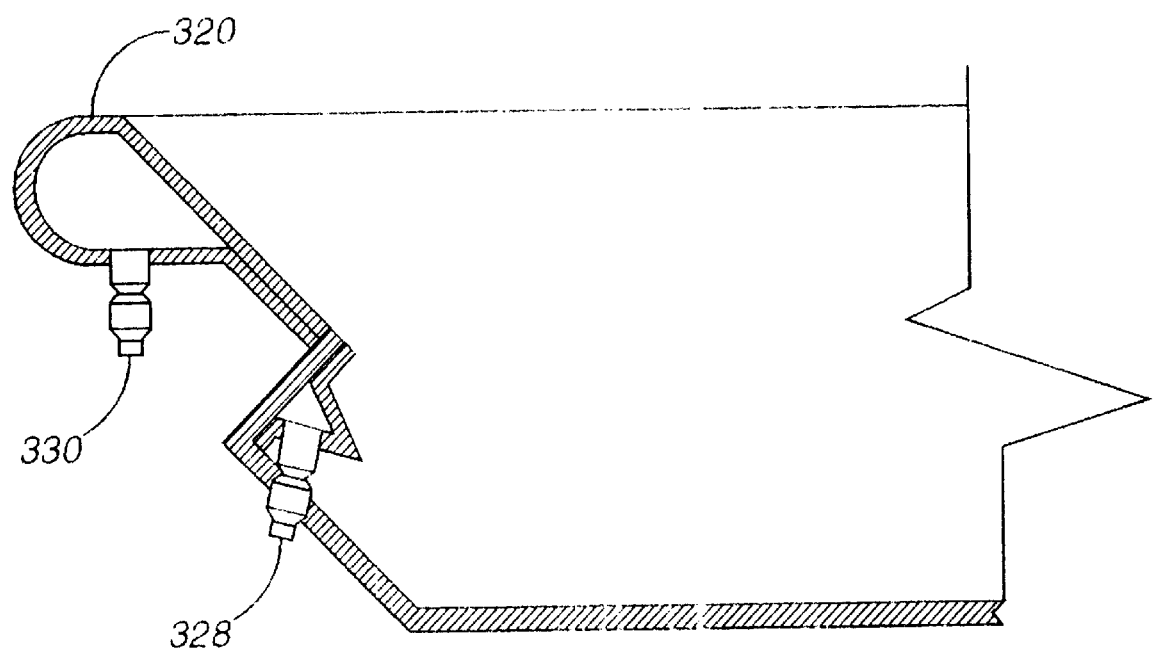
FIG. 13 is a cross section of the tray.

FIGS. 11–13 illustrate preferred embodiments of the invention. The tray 320 is provided with a pair of channels 322 superimposed to the bottom surface thereof, with the channels 322 being spaced apart by a predetermined distance. A plurality of peripherally disposed ventilation and irrigation ducts 324, 326 are provided on the tray 320. A first quick disconnect fitting 328 is provided for directing fluid to the tray 320. A second quick disconnect fitting 330 is provided for removing vapors from the vicinity of the tray 320. A latching mechanism 332 is also provided for securing the autopsy cart 300 to the autopsy station 250, 350. The autopsy cart 300 includes a frame 310 which is formed from a plurality of rigid members. The frame 310 has a generally rectangular shape which defines two long sides and two short sides. The autopsy cart 300 also includes four upstanding legs 312, each of which is attached at one corner of the frame 310 in an vertical manner. Casters 314 are attached to the lower ends of each upstanding leg 312 in order to facilitate movement. A plurality of receptors 316 are secured to the short sides of the frame 310. FIG. 11 illustrates a free standing autopsy station 250 which includes a sink 252 and a faucet assembly 254. The autopsy station 250 is supported by a pedestal 260. The sink 252 and faucet assembly 254 are integrally formed with the pedestal 260. The autopsy station 250 also includes a vacuum means 256 for suctioning vapors from the tray 320 through the ventilation ducts 324. FIG. 12 illustrates a wall mounted autopsy station 350 which includes a sink 352 and a faucet assembly 354. The autopsy station 350 is integrally attached to a wall 370. The sink 352 and the faucet assembly 354 are also integrally attached to the wall 370. The autopsy station 350 also includes a vacuum means 356 for suctioning vapors from the tray 320 through the ventilation ducts 324.

Figure 14:
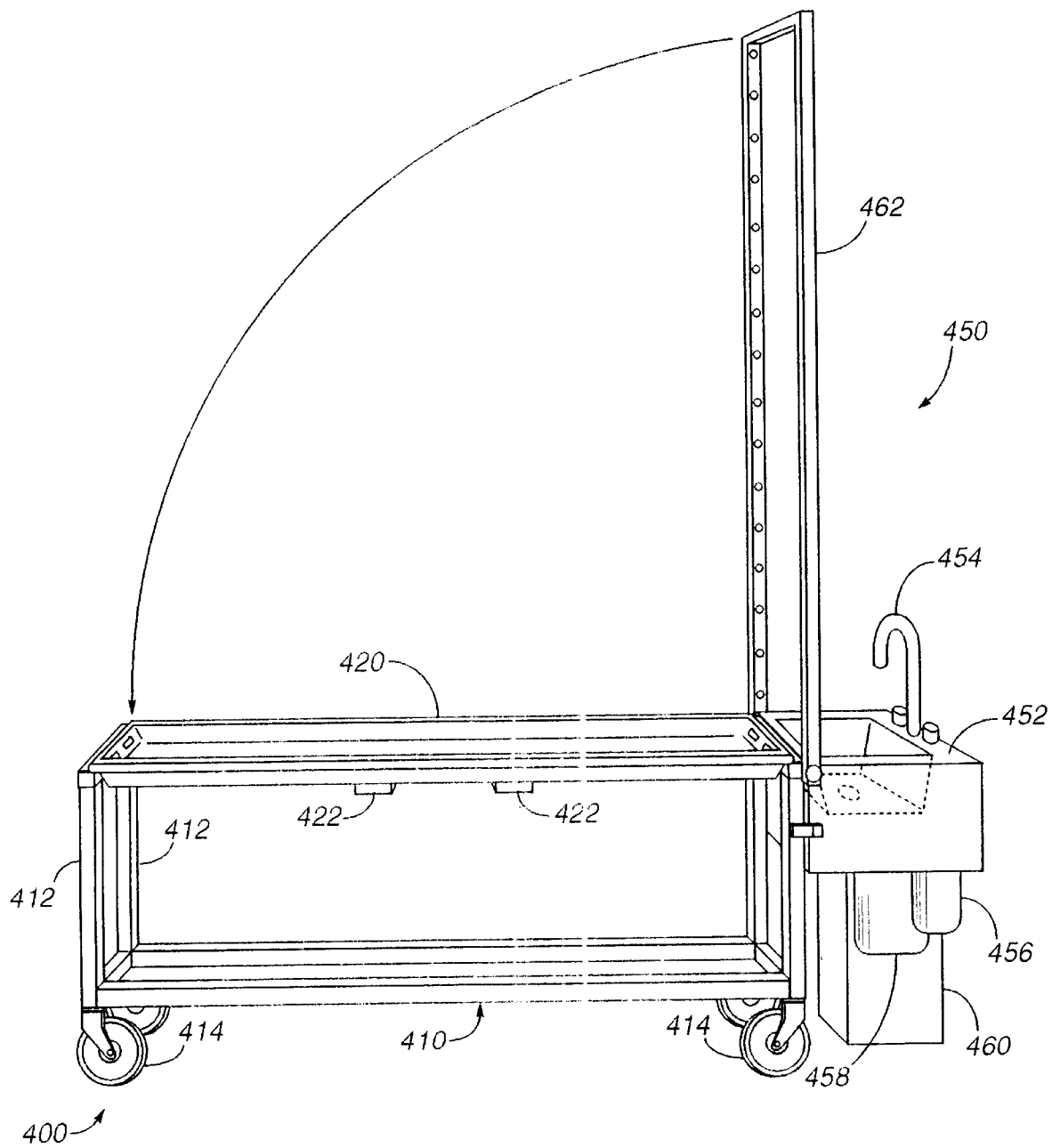
FIG. 14 is a perspective view of an alternative embodiment of an autopsy assembly which includes a free standing autopsy station.
Figure 15:
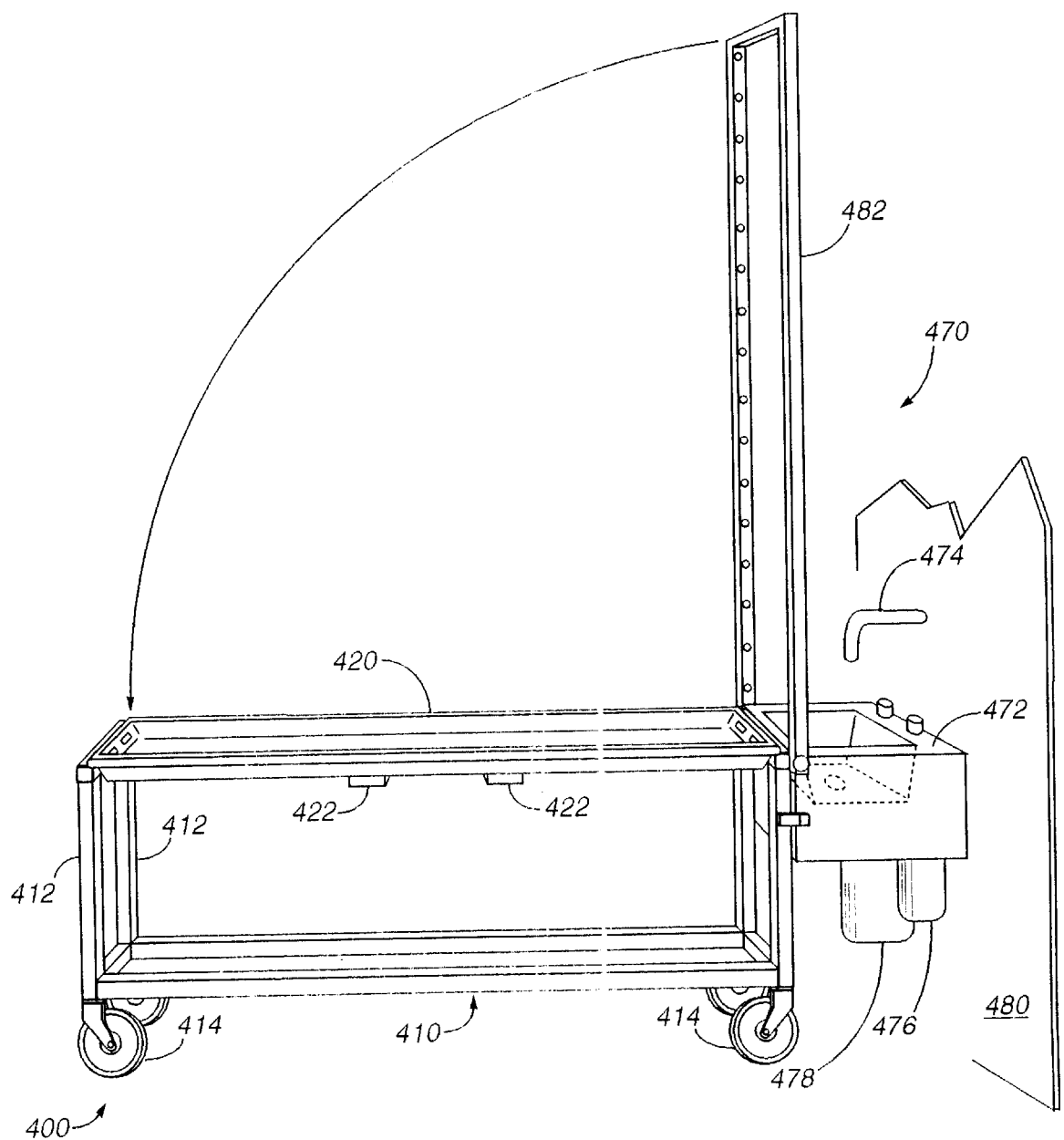
FIG. 15 is a perspective view of an alternative embodiment of an autopsy assembly which includes a wall mounted autopsy station.

FIGS. 14 and 15 illustrate alternative embodiments of the invention wherein the tray 320 is provided with a pair of channels 322 superimposed to the bottom surface thereof, with the channels 322 being spaced apart by a predetermined distance. A latching mechanism 332 is also provided for securing the autopsy cart 300 to the autopsy station 250, 350. The autopsy cart 400 includes a frame 410 which is formed from a plurality of rigid members. The frame 410 has a generally rectangular shape which defines two long sides and two short sides. The autopsy cart 400 also includes four upstanding legs 412, each of which is attached at one corner of the frame 410 in an vertical manner. Casters 414 are attached to the lower ends of each upstanding leg 412 in order to facilitate movement. FIG. 14 illustrates a free standing autopsy station 450 which includes a sink 452 and a faucet assembly 454. The autopsy station 450 is supported by a pedestal 460. The sink 452 and faucet assembly 454 are integrally formed with the pedestal 460. The autopsy station 450 also includes a vacuum means 456 for suctioning vapors from the tray 320 through the ventilation ducts 324. An irrigation rack 462 is swivably mounted to the sink 452. The irrigation rack 462 may be lifted in order to position the autopsy cart 400 and then lowered when the autopsy is to be performed. FIG. 15 illustrates a wall mounted autopsy station 470 which includes a sink 472 and a faucet assembly 474. The autopsy station 470 is integrally attached to a wall 480. The sink 472 and the faucet assembly 474 are also integrally attached to the wall 480. The autopsy station 470 also includes a vacuum means 476 for suctioning vapors from the tray 420. The autopsy station 470 also includes a swivably mounted irrigation rack 482.

Figure 16:
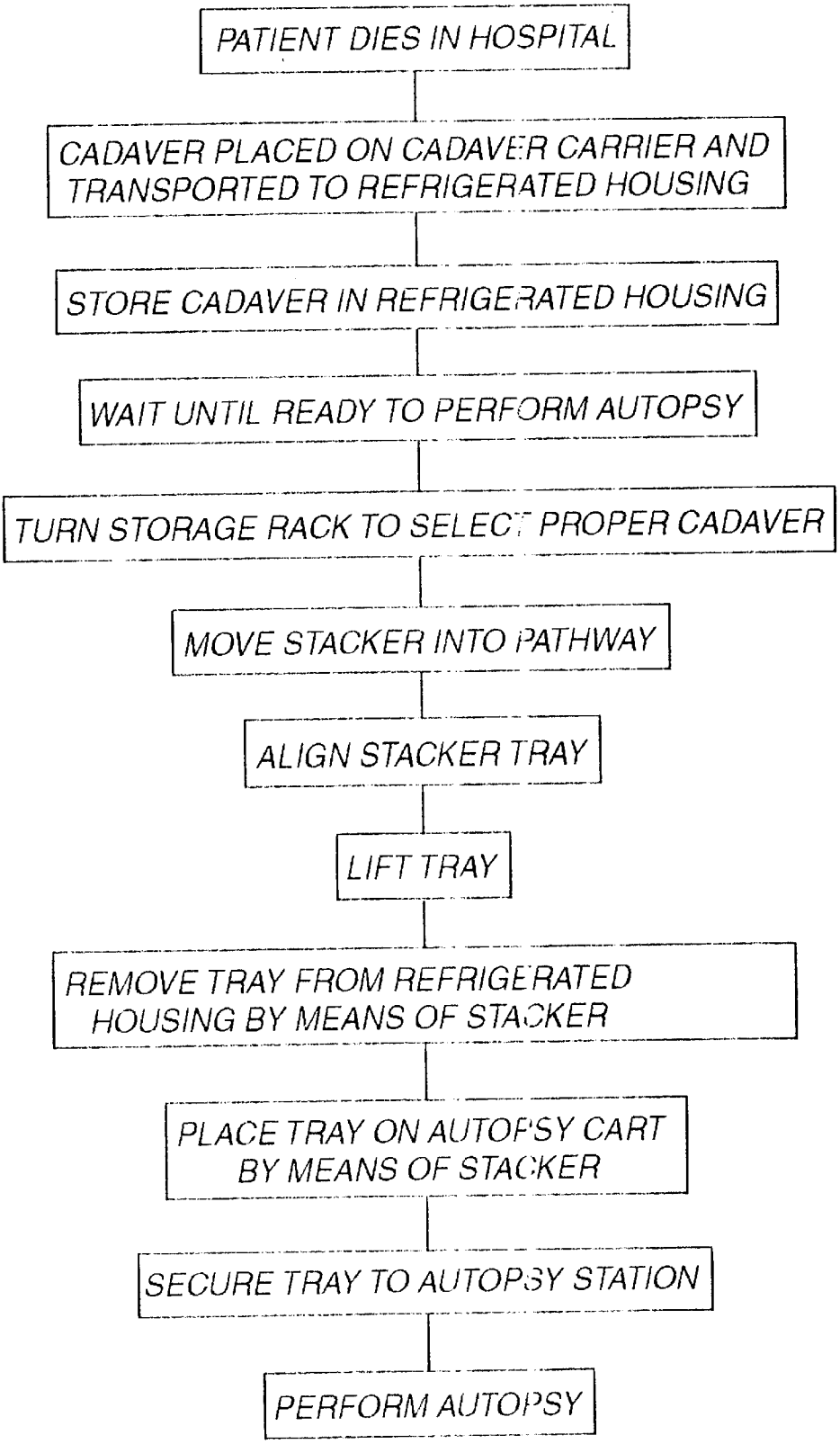
FIG. 16 is a flowchart illustrating the processing of a cadaver in accordance with the present invention.

FIG. 16 outlines the various steps associated with processing the cadaver with the rotational cadaver system 100. The first step of the process is to store the cadaver in a refrigerated housing for a predetermined length of time, or until an appropriate official is ready to perform the autopsy. When appropriate, the cadaver is removed from the refrigerated housing. In order to remove the proper cadaver, it may be necessary to turn the rotational storage stack so that the tray containing the required cadaver is positioned for removal. A switch is used to selectively provide power to the motor thereby turning the rotational storage rack. The stacker is then moved into the pathway of the rotational storage rack and aligned with the tray. The prongs of the stacker are inserted into the channels of the tray and raised vertically so that the tray is lifted from the receptors. Next, the tray containing the cadaver is placed on an autopsy cart. The tray with cadaver is then transported by means of the autopsy cart to the location where the autopsy is to be performed. The autopsy cart is then positioned near a stand alone or wall mounted autopsy station, and secured thereto. Finally, the autopsy is performed.

While the invention has been described with reference to selected preferred embodiments, it should not be limited to those embodiments. Rather, many modifications and variations will become apparent to those skilled in the art without departure from the scope and spirit of this invention as defined in the appended claims. For example, one of ordinary skill in the art will readily appreciate that a second rotational storage rack could be placed in a side by side alignment with a first rotational storage rack, wherein both racks are driven by the same motor.

What is claimed is:

1. A rotational storage rack comprising:
    a base having a hollow interior and a generally rectangular shape and defining two long sides and two short sides,
    a first leg, having opposite ends, vertically positioned at about the midpoint of one of the short sides of said base and secured thereto at one of said ends;
    a second leg, having opposite ends, vertically positioned at about the midpoint of the other short side of said base and secured thereto at one of said ends;
    a first shaft positioned in a horizontal manner proximate to said first leg;
    a second shaft positioned in a horizontal manner proximate to said second leg;
    means for rotatably mounting said first and second shaft respectively to the opposite ends of said first and second legs;
    a spool, having opposite ends, positioned along the centerline of the first and second shafts and each of said ends terminating in an outwardly extending flange;
    a first wheel positioned at one end of said spool proximal to said first leg and secured to one of said outwardly extending flanges;
    a second wheel positioned at the other end of said spool proximal to said second leg and secured to the other of said outwardly extending flanges;
    means for securing said first and second wheels respectively to said first and second shafts;
    a plurality of branches;
    means for securing said branches to said first and second wheels;
    said first and second wheels being secured to said spool in such a manner as to align each branch from said first wheel with a corresponding branch from said second wheel;
    a plurality of arms;
    at least one of said arms pivotally attached to each of said branches, each of said arms remaining substantially vertical while said spool is rotated;
    a plurality of removable trays; and,
    a plurality of hook receptors, fixedly attached to each of said arms opposite the attachment to the branches, for securely receiving each of said trays and supporting said trays in a substantially horizontal manner while said spool is rotated.

2. A rotational storage rack as recited in claim 1 wherein said first and second wheels are secured to the outwardly extending flanges of said spool with threaded fasteners.

3. A rotational storage rack as recited in claim 1 further comprising means for turning said second shaft.

4. A rotational storage each as recited in claim 1 wherein each of said trays contain a plurality of apertures and said plurality of hook receptors is equal in number to said apertures, said hook receptors being capable of insertably engaging said apertures.

5. A rotational storage rack as recited in claim 4 further comprising means for removing said trays from said receptors.

6. A rotational storage rack as recited in claim 5 wherein said means for removing said trays comprises a stacker.

7. A rotational storage rack as recited in claim 6 further comprising means for guiding said stacker so as to facilitate removal of said trays.

8. A rotational storage rack as recited in claim 7 wherein said means for mounting said first and second shafts includes a plurality of bearings.

* * * * *